US00PP26162P3

(12) United States Plant Patent
Egger

(10) Patent No.: US PP26,162 P3
(45) Date of Patent: Nov. 24, 2015

(54) ***HEUCHERA* PLANT NAMED 'BLACK TAFFETA'**

(50) Latin Name: ***Heuchera* hybrid**
Varietal Denomination: Black Taffeta

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 178 days.

(21) Appl. No.: 13/987,220

(22) Filed: Jul. 12, 2013

(65) Prior Publication Data

US 2015/0020279 P1 Jan. 15, 2015

(51) Int. Cl.
*A01H 5/00* (2006.01)

(52) U.S. Cl.
USPC ..... Plt./440

(58) Field of Classification Search
USPC ..... Plt./440
CPC ..... A01H 5/00
See application file for complete search history.

(56) References Cited

PUBLICATIONS

Greenhouse Management, Feb. 12, 2013.*

* cited by examiner

*Primary Examiner* — Keith O. Robinson
(74) *Attorney, Agent, or Firm* — Klarquist Sparkman, LLP

(57) ABSTRACT

A new and distinct *Heuchera* plant substantially as shown and described, characterized by large, shiny, red brown to almost black leaves, very ruffled leaves showing purple backs, a medium large plant size, light pink flowers in spring on short flower stalks, and excellent vigor.

2 Drawing Sheets

Botanical denomination: *Heuchera* hybrid.
Variety designation: 'Black Taffeta'.

BACKGROUND OF THE INVENTION

The present invention relates to a new and distinct cultivar of *Heuchera* and given the cultivar name of 'Black Taffeta'. *Heuchera* is in the family Saxifragaceae. *Heuchera* 'Black Taffeta' originated from a planned cross between *Heuchera* 'K580-8', a proprietary unreleased, unpatented plant, as the seed parent, and *Heuchera* '148-1' as the unpatented pollen parent. Compared to the seed parent, *Heuchera* 'K580-8', the new cultivar has larger leaves that are black rather than blue green. Compared to the pollen parent, *Heuchera* '148-1', the new cultivar has leaves that are larger, black rather than amber colored, and more ruffled, and with pink buds to white flowers rather than insignificant brown.

Compared to *Heuchera* 'Black Beauty' (U.S. Plant Pat. No. 13,288), the new cultivar has a larger habit, larger leaves that are more ruffled.

Compared to *Heuchera* 'Chocolate Ruffles' (U.S. Plant Pat. No. 8,965), the new cultivar has larger, darker, glossier, more ruffled leaves.

Compared to *Heuchera* 'Midnight Ruffles' (U.S. application Ser. No. 13/986,946), the new cultivar has leaves that are glossier, browner, and orbicular rather than ovate, and has flowers that are showy and light pink rather than small and red brown.

Compared to *Heuchera* 'Zipper', U.S. Plant patent application Ser. No. 13/987,219, the new cultivar has a larger habit and foliage color that is red brown to almost black rather than golden amber to orange.

This new *Heuchera* is distinguished by:
1. large, shiny, red brown to almost black leaves,
2. very ruffled leaves showing purple backs,
3. a medium large plant size,
4. light pink flowers in spring on short flower stalks, and
5. excellent vigor.

This new cultivar has been reproduced only by asexual propagation (cuttings and tissue culture). Each of the progeny exhibits identical characteristics to the original plant. Asexual propagation in 2011 by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 2 shows a one year-old *Heuchera* 'Black Taffeta' growing in full sun in the February in the trial bed in Canby, Oreg.

FIG. 3 shows a close up of the flower in May on the new cultivar.

DETAILED PLANT DESCRIPTION

Figure 1:
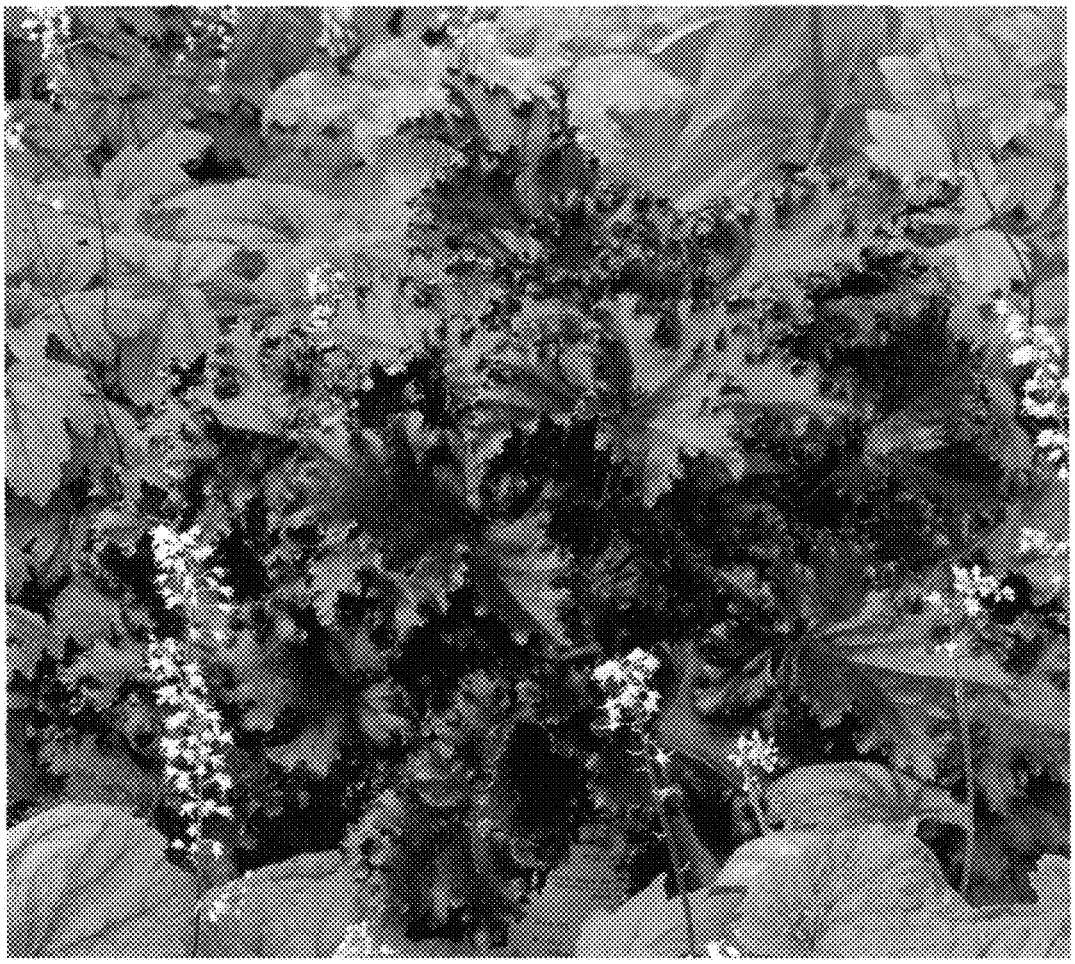
FIG. 1 shows a 9 month-old *Heuchera* 'Black Taffeta' growing in full sun in the garden in summer in Canby, Oreg.

The following is a detailed description of the new *Heuchera* cultivar based on observations of one year-old specimens grown in the ground in the trial bed in shade in May in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition, 2007.

Plant:

*Form.*—Basal rosette, herbaceous perennial.

*Hardiness.*—USDA Zone 4 to 9.

*Size.*—30 cm tall from top of the foliage to the ground and 37 cm wide.

*Habit.*—Mounding.

*Vigor.*—Excellent.

*Roots.*—Fibrous, freely branching, fine, and White 155A in color; roots develop easily from stem cuttings.

Leaf:

*Type.*—Simple.

*Arrangement.*—Basal.

*Shape.*—Orbicular.

*Lobing/division.*—6 main lobes, with 3 to 5 shallow secondary lobes, secondary lobes also lobed.

*Venation.*—Palmate.

*Margins.*—Deeply crenate, moderately undulate and ruffled.

*Apex.*—Mucronulate.

*Base.*—Cordate, lobes overlapping at the base.

*Blade size.*—Grows to 14 cm long and 14 cm wide.

*Surface texture.*—Both sides glandular puberulent, topside moderately glossy.

*Petiole description.*—Grows to 23 cm long and 3 mm wide, glandular puberulent, Greyed Purple 187B.

*Leaf color.*—Variable depending on the time of the year, the temperature, and the exposure; late winter, spring topside between Black 202A and Greyed Purple N187A with veins N187A, bottom side Purple N79A; fall to early winter topside Brown N200A to Grey Brown N199A, bottom side Purple N79A.

Inflorescence:

*Size.*—Grows to 4 cm wide and 30 cm long.

*Type.*—Upright thyrse.

*Number of flowers per thyrse.*—100 to 120 per thyrse.

*Number of thyrse.*—About 8 in spring bloom.

*Peduncle.*—Grows to 24 cm tall, 5 mm wide at base, Greyed Purple 187A, glandular hairs, with 4 to 5 small petiolate leaves (ovate, blades grow to 2 cm long and 2.3 cm wide, 5 main lobes, margin biserrate, topside Greyed Purple 183A, bottom side Red Purple 59A; petioles to 3.5 cm long, glandular puberulent, bottom side Red Purple 59A).

*Pedicel.*—1 to 4 mm long, with glandular hairs, Greyed Purple 187B.

*Bloom period.*—May in Canby, Oreg.

Flower bud:

*Size.*—2 mm wide and 4 mm long.

*Description.*—Glandular puberulent, ovoid.

*Color.*—Top half White N155C, bottom half Greyed Red 181D.

Flower:

*Type.*—Perfect.

*Shape.*—Campanulate.

*Attitude.*—Side to down-facing.

*Size.*—4 mm long and 4 mm wide.

*Petal description.*—5 in number, 3 mm long and less than 1 mm wide, reflexed, spatulate with a clawed base, tip acute, margin entire, glabrous on top and bottom, outside White NN155C, inside White NN155B.

*Calyx description.*—4 mm long and 2 mm wide, with 5 lobes, divided ½ way to the base, glandular hairs on outside, glabrous inside, tip acute, margin entire, outside top White N 155C.

*Stamen description.*—5 in number, each 2.5 mm long, White NN155C, anthers oval and less than 1 mm, Yellow Orange 21C, no pollen, male sterile.

*Pistil description.*—One central two beaked pistil, 3 mm long, Red Purple 70D overall, style 1 mm long, ovary 2 mm long.

*Fragrance.*—None.

*Lastingness.*—Each thyrse blooms for about 2 weeks on the plant.

Fruit:

*Type.*—Two-beaked ovoid capsule.

*Description.*—5 mm long and 5 mm wide, glandular puberulent.

*Fertility.*—Low.

*Color.*—Greyed Brown 199C.

Seed:

*Shape.*—Linear.

*Size.*—2 mm long.

*Color.*—Black 202A.

Disease and pest tolerance: Pest and disease resistance are typical for this type of *Heuchera.*

I claim:

1. A new and distinct *Heuchera* plant as herein illustrated and described.

* * * * *

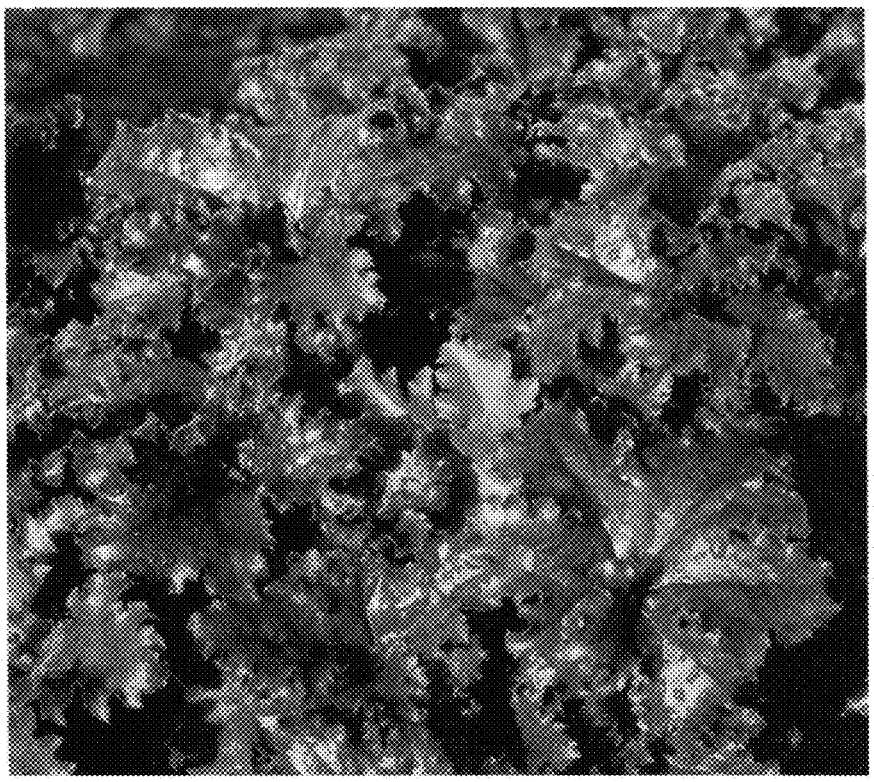
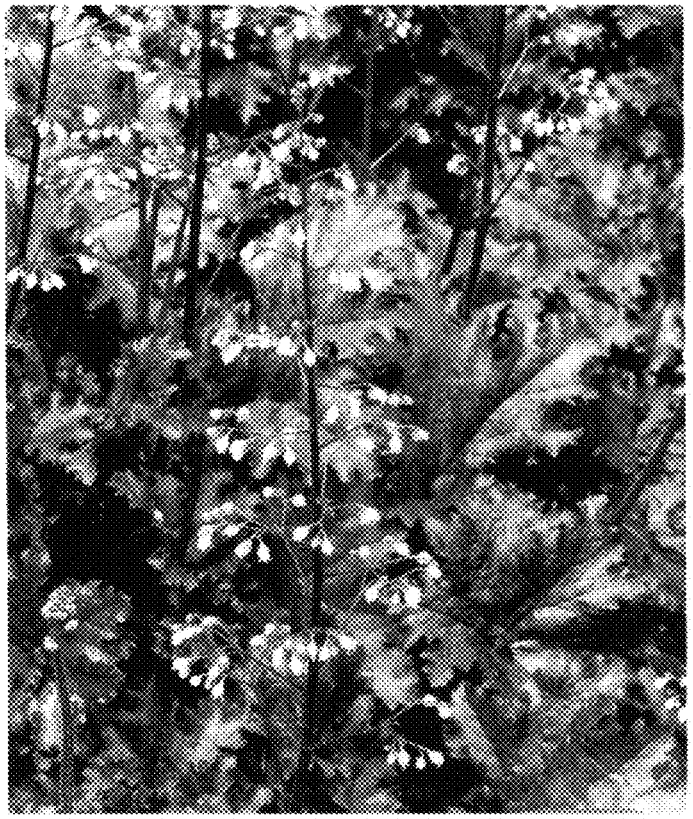
FIG. 2 above,
FIG. 3 on left